United States Patent [19]

Cho et al.

[11] Patent Number: 4,640,922
[45] Date of Patent: Feb. 3, 1987

[54] 3N-SUBSTITUTED 3,4-DIHYDROPYRIMIDINES AS AGENTS FOR TREATING DISORDERS OF CARDIOVASCULAR SYSTEM

[75] Inventors: Hidetsura Cho, Ibaraki; Kazuo Aisaka, Mishima; Mariko Emon, Matsudo, all of Japan

[73] Assignee: Suntory Limited, Osaka, Japan

[21] Appl. No.: 708,887

[22] Filed: Mar. 6, 1985

[30] Foreign Application Priority Data

Mar. 8, 1984 [JP] Japan ................................. 59-44729

[51] Int. Cl.$^4$ .................. A61K 31/505; C07D 239/02
[52] U.S. Cl. ..................................... 514/256; 544/335
[58] Field of Search .......................... 544/335; 514/256

[56] References Cited

U.S. PATENT DOCUMENTS

| | | | |
|---|---|---|---|
| 3,985,758 | 10/1976 | Murakami et al. | 564/312 |
| 4,166,855 | 9/1979 | Wehiyer et al. | 546/321 |
| 4,177,278 | 12/1979 | Bossert et al. | 546/321 |
| 4,293,700 | 10/1981 | Uldrikis et al. | 546/321 |
| 4,520,131 | 5/1985 | Loev et al. | 546/321 |

FOREIGN PATENT DOCUMENTS

| | | |
|---|---|---|
| 0103796 | 3/1984 | European Pat. Off. . |
| 1670827 | 3/1974 | Fed. Rep. of Germany . |
| 81173 | 5/1985 | Japan ................................. 514/256 |

OTHER PUBLICATIONS

Stoltefuss et al., Chem. Abst. 101-55110v.
Cho et al., Chem. Abst. 103-178228p.

*Primary Examiner*—Donald G. Daus
*Assistant Examiner*—Cecilia Shen
*Attorney, Agent, or Firm*—Cushman, Darby & Cushman

[57] ABSTRACT

A 3N-substituted 3,4-dihydropyrimidine derivative of the formula:

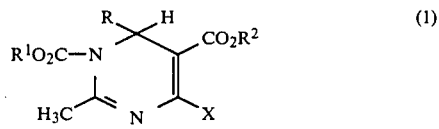

wherein $R^1$ is methyl or ethyl, $R^2$ is methyl or ethyl, R is phenyl or substituted phenyl, X is chloro or methyl and pharmaceutically acceptable acid addition salts thereof have substantially the same strong vasodilative and $Ca^{++}$ antagonistic effects as nicardipine and therefore are useful as agents for treating disorders of the cardiovascular system, for example, hypotensive agents, agents for amelioration of brain circulation and anti-angina pectoris agents.

Processes for producing the above compounds economically and effectively are also disclosed.

4 Claims, No Drawings

3N-SUBSTITUTED 3,4-DIHYDROPYRIMIDINES AS AGENTS FOR TREATING DISORDERS OF CARDIOVASCULAR SYSTEM

TECHNICAL FIELD

This invention relates to 3N-substituted 3,4-dihydropyrimidine derivatives of the formula:

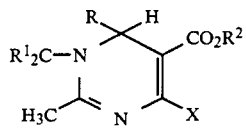

wherein $R^1$ is methyl or ethyl, $R^2$ is methyl or ethyl, R is phenyl or substituted phenyl, X is chloro or methyl and pharmaceutically acceptable salts thereof, processes for preparation thereof and their use as agents for treating disorders of the cariovascular system.

Since the above dihydropyrimidine derivatives of the formula (1) have substantially the same strong vasodilative effects as nicardipine and the effects endure over a long term, said compounds are useful as agents for treating disorders of the cardiovascular system, for example, hypotensors, agents for amelioration of brain circulation and anti-angina pectoris agents.

BACKGROUND ART

Currently it is being found that calcium antagonists ($Ca^{++}$ antagonists), which had been spotlighted as new agents for treating disorders of the cardiovascular system, have a variety of pharmacological effects and are active not only against hypertension, angina pectoris, brain circulation and metabolism incompetence and arrhythmia but also for prevention of arterial sclerosis and increase in effects of carcinostatic agents. Thus indications as to the benefits of $Ca^{++}$ antagonists continue to increase.

$Ca^{++}$ antagonists which have been known include Nifedipine, Nicardipine, Verapamil, Diltiazen and the like. But there is room for improvement in the properties of the above-mentioned known $Ca^{++}$ antagonists such as duration, organ-selectivity, stability against light, heat etc. and side effects. Up to this day, however, dihydropyrimidine derivatives have not often been investigated. Only a few references disclose said derivatives. [For example refer to Silversmith, E. F. J., Org. Chem., 27, 14090 (1962), Nasipuri, D. et al., Synthesis 1073 (1982), Kashima, C., Tetrahedron Letters 209 (1982) and Japanese Patent Public Disclosure No. 73572/59 (Bayer, A.B.)]

This can be considered to be due to the instability and tautomerism of the hydropyrimidine derivatives.

SUMMARY OF THE INVENTION

The inventors eagerly investigated the $Ca^{++}$ antagonists which are currently considered to be important. As a result we found that N-substituted 3,4-dihydropyrimidine derivatives of the formula (1) have excellent vasodilative effects.

The present invention provides N-substituted 3,4-dihydropyrimidine derivatives of the formula (1) and pharmaceutically acceptable acid addition salts thereof and processes for preparation of the same.

Dihydropyrimidine derivatives of the formulae:

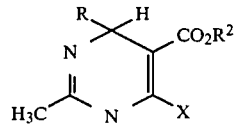

and

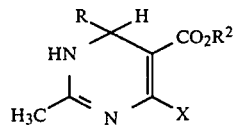

wherein R, $R^2$ and X are as defined above, and which are tautomeric isomers, have vasodilative effects too. But the compounds of the formula (1) were synthesized in order to obtain compounds having higher stability and activity.

DETAILED DESCRIPTION OF THE INVENTION 3N-substituted 3,4-dihydropyrimidine derivatives of the formula (1) can be prepared in the following procedures:

(i) 6-methyl-dihydropyrimidine (2) and (2')

An α,β-unsaturated carbonyl compound of the formula (3):

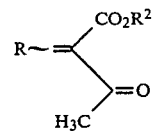

wherein $R^2$ is methyl or ethyl and R is phenyl or substituted phenyl is reacted with not less than one equivalent of acetamidine in a suitable alcohol to obtain a tetrahydropyrimidine derivative of the formula:

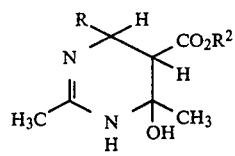

wherein R and $R^2$ are as defined above. When using a salt of acetamidine such as a hydrochloride, it is preferable to convert acetamidine with alkali metal alkoxide to a free amine before forming the salt. Alcohols used in the above reaction preferably include methanol and ethanol.

The thus obtained tetrahydropyrimidine derivatives (4) can be converted to dihydropyrimidine derivatives of the formulae (2) and (2') after purification as hydrochlorides of the compounds (4) or without purification.

Processes for preparing compounds (2) and (2') from compounds (4) include, for example, Process A comprising dehydrating a compound (4) by heating with p-toluenesulfonic acid, benzenesulfonic acid or the like; Process B comprising mixing a compound (4) with not less than about 5 parts by weight, preferably about 10 parts by weight of an inorganic substance such as alumina, silica gel or molecular sieve, heating the mixture at 120°–200° C. for 15 minutes to 1 hour and extracting the mixture with an organic solvent; and Process C comprising dissolving the compound (4) in phosphorus oxychloride and dehydrating said compound by heating the solution to reflux.

According to the above Processes A, B and C, the dihydropyrimidine derivatives of the formulae (2) and (2') can be obtained in a yield of 40–70%, 20–50% and about 50%, respectively. The derivatives (2) and (2') can also be obtained by dehydrating compounds (4) by using an acid such as camphor-10-sulfonic acid or a lewis acid such as boron trifluoride ether complex.

The product can be purified by conventional methods such as adsorption chromatography, evaporation, recrystallization, etc. Alternatively the product can be crystallized as an inorganic acid salt thereof such as hydrochloride, sulfate or phosphate or an organic acid salt thereof such as oxalate, tartarate, succinate or maleate, and then purified by recrystallization.

The above procedures can be illustrated by the following scheme:

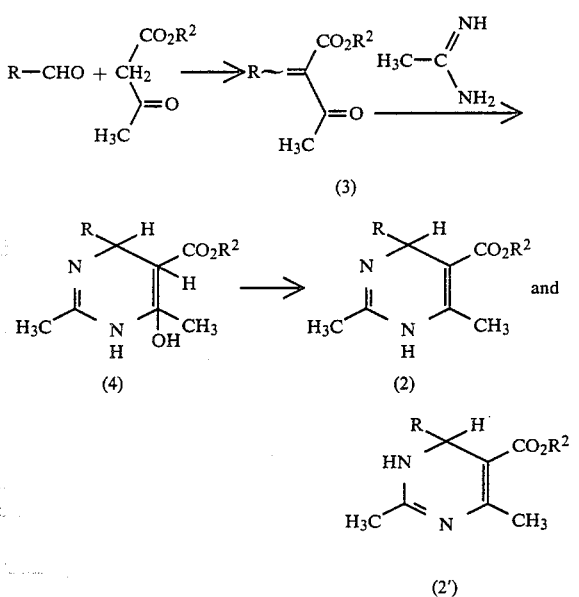

wherein $R^2$ is methyl or ethyl, and R is phenyl or substituted phenyl.

(ii) 6-chloro-dihydropyrimidine (2) and (2')

5,6-Dihydro-4-pyrimidine (5) of the formula:

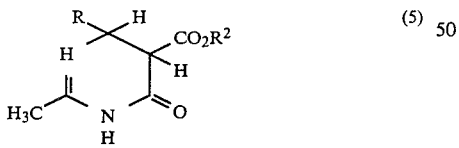

wherein $R^2$ is methyl or ethyl and R is phenyl or substituted phenyl is heated with phsophorus oxychloride or phosphorus pentachloride. The reaction can be carried out in an inert organic solvent but preferably no solvent is used.

5,6-Dihydro-4-pyrimidine of the formula (5) can be synthesized by an improved process which is a modification of a process described in the reference [C. D. H. Allen et al., Org. Syn. Coll. Vol. 3, 377 (1955)]. First, dialkyl malonate is heated with an equivalent of an aldehyde in the presence of a base such as piperidine, methylpiperidine or trialkylamine in a solvent, peferably aromatic hydrocarbon, ether, halogenized hydrocarbon to produce 2-alkoxycarbonylpropenic acid ester of the formula:

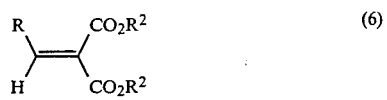

wherein $R^2$ is methyl or ethyl and R is phenyl or substituted phenyl. Purification of the ester (6) can be carried out by conventional methods such as distillation, recrystallization, column chromatography or thin layer chromatography to obtain crystals or oil.

Next, propenic acid ester (6) is heated with an equivalent of acetamidine or a salt thereof in an alcohol in the presence of an alkali metal alcoholate such as lithium ethoxide, sodium ethoxide, potassium ethoxide, sodium methoxide, lithium methoxide, sodium propoxide, potassium propoxide, potassium butoxide or the like to produce 5,6-dihydro-4-pyrimidine of the formula (5). The thus obtained 5,6-dihydro-4-pyrimidine (5) is easily purified by conventional methods such as distillation, recrystallization, adsorption chromatography, partition chromatography, gel filtration, or methods utilizing solubility or acidity.

The dihydropyrimidine derivatives of the formulae (2) and (2') which are tautomeric isomers can be obtained by heating 5,6-dihydro-4-pyrimidines of the formula (5) with an excess of phosphorus oxychloride or phosphorus pentachloride. After the reaction is quenched by adding water to the reaction mixture to decompose the phosphorus compound or by removing said reagent by distillation, the residue is extracted with an organic solvent to isolate the object compound as pure crystals or oil. Alternatively the crude product is purified by conventional methods such as silica gel chromatography (adsorption chromatography), partition chromatography, gel filtration chromatography, recrystallization, distillation, etc. The dihydropyrimidine derivatives of the formulae (2) and (2') form salts with an inorganic acid such as hydrochloric acid or sulfate or an organic acid such as oxalic acid or succinic acid.

The above procedures can be illustrated as follows:

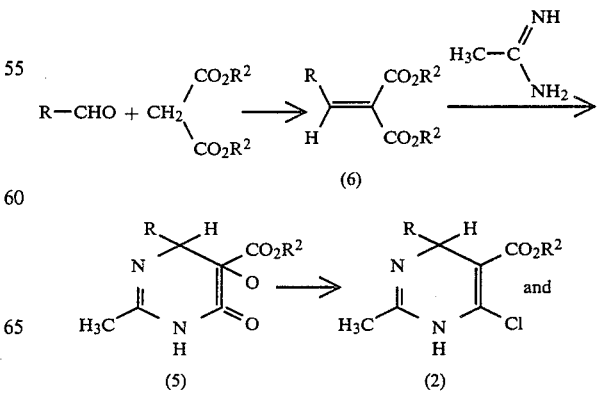

-continued

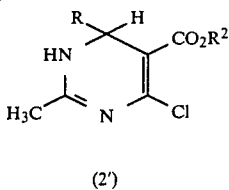

(2')

wherein R² is methyl or ethyl and R is phenyl or substituted phenyl.

(iii) 3N-substituted 3,4-dihydropyrimidine derivatives

A compound represented by the formulae (2) and (2') is dissolved in an organic solvent such as hydrocarbon chloride, aromatic hydrocarbon, ether or the like and treated with a compound of the formula

or $(R^1O)_2C=O$, wherein $R^1$ is $CH_3$ or $C_2H_5$ in the presence of a base e.g. trialkylamine, sodium hydride, potassium hydride or triethylene to produce a 3N-substituted 3,4-dihydropyrimidine derivative of the formula (1).

Alternatively a compound represented by the formulae (2) and (2') is converted with sodium hydride, potassium hydride, alkyl lithium or lithium hydride to a alkali metal salt thereof and the salt is treated with a compound of the formula

or $(R^1O)_2C=O$, wherein $R^1$ is $CH_3$ or $C_2H_5$ to produce a 3N-substituted 3,4-dihydropyrimidine derivative of the formula (1).

After the above reaction the products of the formula (1) of this invention can be purified by using conventional methods such as adsorption column chromatography, ion-exchange chromatography or recrystallization. Alternatively, the products can be treated with an inorganic acid such as hydrochloric acid, sulfuric acid or phosphoric acid, or an organic acid such as oxalic acid, succinic acid or malic acid to convert them to salts thereof, and then can be purified by recrystallization, adsorption chromatography or ion-exchange chromatography.

The thus obtained compounds of the formula (1) indicated strong vasodilative effects in Langendorff's method and showed strong vasodilative and hypotensive effects in pharmacological tests using anesthetized dogs.

The processes of this invention are illustrated by the following scheme:

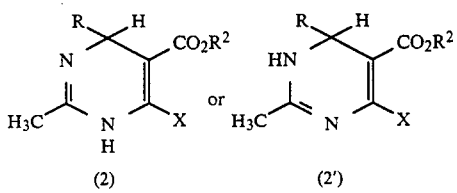

-continued

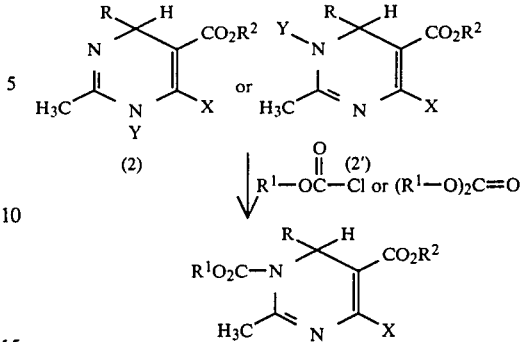

wherein $R^1$ is methyl or ethyl, $R^2$ is methyl or ethyl, R is phenyl or substituted phenyl, and Y is an alkali metal.

The thus synthesized 3N-substituted 3,4-dihydropyrimidine derivatives of the formula (1) are exemplified as follows:

1. 5-Alkoxycarbonyl-3-N-methoxycarbonyl-2,6-dimethyl-4-phenyl-3,4-dihydropyrimidine
2. 5-Alkoxycarbonyl-3-N-ethoxycarbonyl-2,6-dimethyl-4-phenyl-3,4-dihydropyrimidine
3. 5-Alkoxycarbonyl-3-N-methoxycarbonyl-2,6-dimethyl-4-(nitrophenyl)-3,4-dihydropyrimidine
4. 5-Alkoxycarbonyl-3-N-ethoxycarbonyl-2,6-dimethyl-4-(nitrophenyl)-3,4-dihydropyrimidine
5. 5-Alkoxycarbonyl-3-N-methoxycarbonyl-2,6-dimethyl-4-(chlorophenyl)-3,4-dihydropyrimidine
6. 5-Alkoxycarbonyl-3-N-ethoxycarbonyl-2,6-dimethyl-4-(chlorophenyl)-3,4-dihydropyrimidine
7. 5-Alkoxycarbonyl-3-N-methoxycarbonyl-2,6-dimethyl-4-(bromophenyl)-3,4-dihydropyrimidine
8. 5-Alkoxycarbonyl-3-N-ethoxycarbonyl-2,6-dimethyl-4-(bromophenyl)-3,4-dihydropyrimidine
9. 5-Alkoxycarbonyl-3-N-methoxycarbonyl-2,6-dimethyl-4-(fluorophenyl)-3,4-dihydropyrimidine
10. 5-Alkoxycarbonyl-3-N-ethoxycarbonyl-2,6-dimethyl-4-(fluorophenyl)-3,4-dihydropyrimidine
11. 5-Alkoxycarbonyl-3-N-methoxycarbonyl-2,6-dimethyl-4-(methylthiophenyl)-3,4-dihydropyrimidine and
12. 5-Alkoxycarbonyl-3-N-ethoxycarbonyl-2,6-dimethyl-4-(methylthiophenyl)-3,4-dihydropyrimidine.

In the above compounds 1–18, "alkoxy" means methoxy or ethoxy and "nitrophenyl", "chlorophenyl", "bromophenyl", "fluorophenyl" or "methylthiophenyl" includes phenyl groups which are substituted with $NO_2$, Cl, Br, F or $CH_3S$ at the position 2, 3 or 4 of the phenyl ring, respectively.

The compounds of the formula (1) having ethyl group or propyl group at the position 2 can be prepared by using propylamidine or butylamidine in place of acetamidine.

Those skilled in the art will easily understand that the compounds of the formula (1) wherein R is trifluoromethylphenyl, dichlorophenyl, loweralkylphenyl and lower-alkoxyphenyl can also be obtained by the processes of the present invention.

That is, the compounds of this invention have excellent coronary-vasodilative effects in guinea pigs, increase blood flow through the vertebral arteries of dogs and reduce the resistance of vertebral arteries and systemic blood pressure in dogs. Thus, the compounds are useful as agents for treating coronary impairments, brain circulation incompetence and hypertension.

The compounds (1) of this invention can be administered alone or in combination with excipients in a variety of dosage forms such as tablets, troches, pills, granules, powders, capsules, ampules, suppositories and the like. The excipients include, for example, starch, dexstrin, sucrose, lactose, silic acid, carboxymethylcellulose, cellulose, geratin, polyvinylpyrrolidone, glycerin, agar, calcium carbonate, sodium bicarbonate, paraffin, cetyl alcohol, stearic acid esters, kaolin, bentonite, talc, calcium stearate, magnecium stearate, polyethyleneglycol, water, ethanol, isopropyl alcohol, propyleneglycol and the like.

For parenteral administration, the compounds of this invention are converted into water soluble salts thereof and the salts are dissolved in sterile distilled water or sterile physiological saline and are filled in ampules to be used for injection. If necessary, stabilizing agents and/or buffering agents can be included in the ampules.

For oral administration, the optimum dose range of the compound (1) of this invention is 0.5–500 mg per day. Of course, this dose range can be suitably changed depending upon the characteristics of the subjects including age, response, weight, severity of disease etc.

This invention can be illustrated by the following examples but it should be understood that it is not limited to them. The temperatures stated are in °C. unless otherwise specified.

PREPARATION 1

5-Ethoxycarbonyl-6-chloro-2-methyl-4-phenyl-1,4-dihydropyrimidine and 5-ethoxycarbonyl-6-chloro-2-methyl-4-phenyl-3,4-dihydropyrimidine Ten ml of phosphorus oxychloride was added to 200 mg (0.77 millimole) of 5-ethoxycarbonyl-2-methyl-6-phenyl-5,6-dihydro-4-pyrimidine (m.p. 129°–131°) and the mixture was heated for 20 minutes to reflux. Excess phosphorus oxychloride was evaporated under reduced pressure and chloroform was added to the residue. A saturated aqueous potassium carbonate solution was added to the residue with stirring in ice, the chloroform layer was separated and the aqueous layer was further extracted with chloroform. After extraction with chloroform, the obtained oil was purified on silica gel by column chromatography and recrystallized from ether/acetone.

| | |
|---|---|
| Amount of phosphorus oxychloride (ml) | 10 |
| Reaction time (min) | 20 |
| Yield (yield in %) | 126 mg (60) |
| Purification and properties | Recrystallized from ether/acetone m.p. 155–156° (HCl salt 175–178.5°) |
| N—NMR (CDCl$_3$) (δ ppm) | 1.13(3H, t, J = 8 Hz), 1.86(3H, s), 3.99(2H, q, J = 8 Hz), 5.50(1H, s), 7.27(5H, s) |
| IR spectrum (cm$^{-1}$) | 3430, 1710, 1680 (CHCl$_3$) |
| Mass spectrum (m/z) | 278 (M$^+$) |
| Analysis | Calculated for C$_{14}$H$_{16}$Cl$_2$N$_2$O$_2$ as HCl salt: C 53.34; H 5.12; N 8.89 Found: C 53.13; H 5.07; N 8.87 |

PREPARATION 2

5-Ethoxycarbonyl-2,6-dimethyl-4-phenyldihydropyrimidine 625 mg of 5-ethoxycarbonyl-6-hydroxy-2,6-dimethyl-4-phenyl-1,4,5,6-tetrahydropyrimidine was dissolved in 5 ml of anhydrous benzene. To the solution 472 mg of paratoluene sulfonic acid was added and the mixture was refluxed for 1.5 hours. Almost all the benzene was evaporated and the residue was diluted with a saturated aqueous potassium carbonate solution and extracted with chloroform. The organic layer was dried with anhydrous potassium carbonate and the solvent was evaporated under reduced pressure to obtain 572 mg of the residue. It was subjected to aluminum (Wako Junyaku K.K.) column chromatography and eluted with a mixture of chloroform and benzene 1:1 and then chloroform to obtain 398 mg of title product. The product was dissolved in ethanol and treated with a saturated etheric HCl to produce a hydrochloride of the title product.

Properties:
Colorless crystals.
m.p. 156°–157° (recrystallized from ether/hexane).
IR spectrum (CHCl$_3$, cm$^{-1}$): 3440, 1695.
$^1$H-NMR spectrum (DMSO-d$_6$, ppm): 1.08(3H, t, J=7 Hz), 1.86(3H, s), 2.20(3H, s), 3.95(2H, q, J=7 Hz), 5.33(1H, s), 7.15–7.30(5H, m).
Properties of the hydrochloride:
m.p. 209°–211° (recrystallized from ethanol/ether).
Analysis: Calculated for C$_{15}$H$_{19}$ClN$_2$O$_2$: C 61.12; H 6.50; N 9.50 (%). Found: C 61.14; H 6.52; N 9.34 (%).

PREPARATION 3

5-Ethoxycarbonyl-2,6-dimethyl-4-(3-nitrophenyl)dihydropyrimidine 150 mg of 5-ethoxycarbonyl-6-hydroxy-2,6-dimethyl-4-(3-nitrophenyl)-1,4,5,6-tetrahydropyrimidine was dissolved in 14 ml of phosphorus oxychloride and the solution was heated to reflux for 30 minutes. After phsophorus oxychloride was evaporated under reduced pressure, a saturated aqueous potassium carbonate solution was added to the residue and the mixture was extracted with chloroform. After the chloroform layer was dried with anhydrous potassium carbonate, the solvent was evaporated to produce 72 mg of the title compound.

Properties:
IR spectrum (CHCl$_3$, cm$^{-1}$): 3440, 1690.
$^1$H-NMR spectrum (CDCl$_3$, ppm): 1.18(3H, t, J=7 Hz), 2.05(3H, s), 2.37(3H, s), 4.09(2H, q, J=7 Hz), 5.67(1H, s), 7.40–8.20(4H, m).
Properties of the HCl salt:
m.p. 223°–226° (recrystallized from methanol/ether).
Analysis: Calculated for C$_{15}$H$_{18}$ClN$_3$O$_4$: C 53.02; H 5.34; N 12.37 (%). Found: C 53.12; H 5.28; N 12.24 (%).

EXAMPLE 1

2,6-Dimethyl-5-ethoxycarbonyl-3-N-ethoxycarbonyl-4-(2'-nitrophenyl)-3,4-dihydropyrimidine To a solution of 5-ethoxycarbonyl-2,6-dimethyl-4-(2'-nitrophenyl)-dihydropyrimidine (756 mg, 2.49 millimole) and triethylamine (374 mg, 3.7 millimole) in 30 ml of chloroform ethyl chlorocarbonate (406 mg, 3.74 millimole) was added dropwise with stirring in ice and the mixture was stirred at room temperature for 3 hours. The reaction mixture was washed with 2% aqueous NaOH solution and water, dried and evaporated to remove the solvent. The obtained oil (730 mg) was purified on silica gel by column chromatography and eluted with 1% MeOH/CHCl$_3$ to obtain the title product as crystals. The crystals were recrystallized from acetone-n-hexane to obtain colorless prisms (m.p. 130°–131.5°, 290 mg, 31% yield).

IR spectrum (CHCl$_3$, cm$^{-1}$): 1730, 1710.

NMR spectrum (CDCl$_3$,): 1.22(3H, t, J=7 Hz), 1.33(3H, t, J=7 Hz), 2.35(3H, s), 2.45(3H, d, J=1 Hz), 4.1–4.5(4H, m), 6.87(1H, d, J=1 Hz), 7.4–7.6(3H, m), 7.76–7.90(1H, m).

Analysis: Calculated for C$_{18}$H$_{21}$N$_3$O$_6$: C 57.59; H 5.64; N 11.20 (%). Found: C 57.76; H 5.62; N 11.11 (%).

EXAMPLE 2

6-Chloro-5-ethoxycarbonyl-3-N-methoxycarbonyl-2-methyl-4-(3′-nitrophenyl)-3,4-dihydropyrimidine To a solution of 6-chloro-5-ethoxycarbonyl-2-methyl-4-(3′-nitrophenyl)-dihydropyrimidine (0.5 g, 1.54 millimole) and triethylamine (1.6 g, 16 millimole) in 20 ml of chloroform 1.46 g (15.4 millimole) of methyl chloroformate was added dropwise with stirring in ice and the mixture was stirred at room temperature for 3 hours. The reaction solution was washed with 2% aqueous NaOH solution and then water, dried and evaporated to obtain 0.5 g of the title product as oil.

The oil was purified on solica gel by column chromatography to obtain the title product as crystals (163 mg, 28% yield). The crystals were recrystallized from acetone-n-hexane to obtain light yellow crystals.

Properties:

Light yellow prismatic crystals.

m.p. 113°–114°.

IR spectrum (CHCl$_3$, cm$^{-1}$): 1730, 1690.

NMR spectrum (CDCl$_3$, ): 1.28(3H, g, J=7 Hz), 2.49(3H, s), 3.94(3H, s), 4.24(2H, m), 6.39(1H, s), 7.52(1H, t, J=8 Hz), 7.64(1H, d, J=8 Hz), 8.17(1H, s), 1.81(1H, d, J=8 Hz).

Analysis: Calculated for C$_{16}$H$_{16}$ClN$_3$O$_6$: C 50.33; H 4.22; N 11.01 (%). Found: C 50.73; H 4.26; N 10.94 (%).

EXAMPLE 3

2,6-Dimethyl-5-ethoxycarbonyl-3-N-methoxycarbonyl-4-(3′-nitrophenyl)-3,4-dihydropyrimidine To a solution of 2,6-dimethyl-5-ethoxycarbonyl-4-(3′-nitrophenyl)-dihydropyrimidine (0.64 g, 2.1 millimole) and triethylamine (0.32 g, 3.2 millimole) in 30 ml of chloroform methyl chlorofomate (0.3 g, 3.16 millimole) was added dropwise with stirring in ice. The mixture was stirred at room temperature for one hour and treated in the same manner as Examples 1 and 2 to obtain 0.6 g of oil. The oil was purified on silica gel by column chromatography to obtain 0.56 g (74% yield) of the title product.

The purified oil was dissolved in a small amount of ethanol and excess ether saturated with hydrogen chloride gas was added to the solution to obtain a HCl salt of the title product. It was recrystallized from ethanol/ether to obtain crystals.

Properties: Oil

IR spectrum (CHCl$_3$, cm$^{-1}$): 1730, 1710.

NMR spectrum (CDCl$_3$): 1.25(3H, t, J=7 Hz), 2.41(3H, s), 2.45(3H, s), 3.91(3H, s), 4.20(2H, m), 6.26(1H, s), 7.48(1H, t, J=8 Hz), 7.60(1H, d, J=8 Hz), 8.13(1H, s), 8.14(1H, d, J=8 Hz).

Analysis: Calculated for C$_{17}$H$_{20}$ClN$_3$O$_6$: C 51.32; H 5.07; N 10.56 (%). Found: C 51.45; H 5.12; N 10.50 (%).

Properties of HCl salt: Colorless prisms m.p. 106.5°–108°.

In the following examples products of the formula (1) were obtained according to the above method:

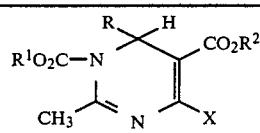

(1)

| Comp. (Ex. No.) | (1) Chemical structure | Yield (%) | Properties (m.p., recrystallization solvents) | IR spectrum (CHCl$_3$, cm$^{-1}$) | NMR spectrum (CDCl$_3$, δ) | ① Analysis ② High resolution mass spectrum |
|---|---|---|---|---|---|---|
| 4 | R$^1$ = R$^2$ = ethyl<br>X = chloro<br>R = 2-nitrophenyl | 44 | oil | 1740, 1720 | 1.24(3H,t,J=7Hz), 1.32(3H,t,J=7Hz), 2.44(3H,s), 4.10–4.35 (4H,m), 7.01(1H,s), 7.43–7.62 (3H,m), 7.83(1H,d,J=8Hz) | ① Calculated for C$_{17}$H$_{18}$ClN$_3$O$_6$:<br>C(%) H(%) N(%)<br>51.58 4.58 10.62<br>Found: 51.88 4.58 10.65 |
| 5 | R$^1$ = methyl<br>R$^2$ = ethyl<br>X = methyl<br>R = 2-nitrophenyl | 34 | crystals 110–111° (acetone. n-hexane) | 1740, 1700 | 1.23(3H,t,J=7Hz), 2.34(3H,s), 2.46(3H,d,J=1Hz), 3.79(3H,s), 4.20(2H,q,J=7Hz), 6.81(1H,d, J=1Hz), 7.4–7.6(3H,m), 7.74–7.88(1H,m) | ① Calculated for C$_{17}$H$_{19}$N$_3$O$_6$:<br>C(%) H(%) N(%)<br>56.50 5.30 11.63<br>Found: 56.76 5.33 11.44 |
| 6 | R$^1$ = methyl<br>R$^2$ = ethyl<br>X = chloro<br>R = 2-nitrophenyl | 28 | crystals 100–102° (benzene n-hexane) | 1745, 1720 | 1.24(3H,t,J=7Hz), 2.43(3H,s), 3.81(3H,s), 4.20(2H,m), 6.95(1H,s), 7.43–7.62(3H,m), 7.81(1H,d,J=8Hz) | ① Calculated for C$_{16}$H$_{16}$ClN$_3$O$_6$,<br>C(%) H(%) N(%)<br>50.33 4.22 11.01<br>Found: 50.56 4.25 11.02 |
| 7 | R$^1$ = ethyl<br>R$^2$ = methyl<br>X = methyl<br>R = 2-nitrophenyl | 76 | crystals 128–129° (ethyl acetate. n-hexane) | 1730, 1715 | 1.33(3H,t,J=7Hz), 2.37(3H,s), 2.45(3H,s), 3.70(3H,s), 4.26(2H,m), 6.84(1H,s), 7.38–7.52(3H,m), 7.75(1H,d,J=8Hz) | ② Calculated for C$_{17}$H$_{19}$N$_3$O$_6$:<br>361.1272<br>Found: 361.1226 |
| 8 | R$^1$ = R$^2$ = ethyl<br>X = methyl<br>R = 2-bromophenyl | 61 | crystals 74° (n-hexane) | 1730, 1710 | 1.24(3H,t,J=7Hz), 1.36(3H,t,J=7Hz), 2.41(3H,s), 2.42(3H,s), 4.16(2H,q,J=7Hz), 4.23–4.37 (2H,m), 6.52(1H,s), 7.05–7.32 (3H,m), 7.54(1H,d,J−8Hz) | ① Calculated for C$_{18}$H$_{21}$BrN$_2$O$_4$:<br>C(%) H(%) N(%)<br>52.82 5.17 6.85<br>Found: 52.89 5.13 6.87 |
| 9 | R$^1$ = ethyl<br>R$^2$ = methyl<br>X = chloro | 38 | oil | 1740, 1725 | 1.33(3H,t,J=7Hz), 2.46(3H,s), 4.26(2H,m), 6.98(1H,s), 7.42–7.62(3H,m), | ② Calculated for C$_{16}$H$_{16}$ClN$_3$O$_6$:<br>381.0149 |

-continued

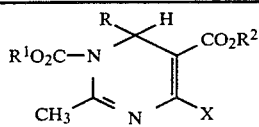
(1)

| Comp. (Ex. No.) | (1) Chemical structure | Yield (%) | Properties (m.p., recrystallization solvents) | IR spectrum (CHCl₃, cm⁻¹) | NMR spectrum (CDCl₃, δ) | ① Analysis ② High resolution mass spectrum |
|---|---|---|---|---|---|---|
| 10 | R¹ = R² = X = methyl<br>R = 2-nitrophenyl | 38 | crystals 137–138° (ethyl acetate. n-hexane) | 1740, 1710 | 7.82(1H,d,J=8Hz) 2.37(3H,s), 2.45(3H,brs), 3.70(3H,s), 3.79(3H,s), 6.78(1H,brs), 7.38–7.54(3H,m), 7.73(1H,d,J=8Hz) | Found: 381.0149<br>② Calculated for C₁₆H₁₇N₃O₆:<br>347.1118<br>Found: 347.1121 |
| 11 | R¹ = R² = methyl<br>X = chloro<br>R = 2-nitrophenyl | 21 | oil | 1745, 1730 | 2.45(3H,s), 3.69(3H,s), 3.74(3H,s), 6.93(1H,s), 7.45–7.12(3H,m), 7.79(1H,d,J=8Hz) | ② Calculated for C₁₅H₁₄ClN₃O₆:<br>367.0569<br>Found: 367.0313 |
| 12 | R¹ = R² = ethyl<br>X = methyl<br>R = 3-nitrophenyl | 92 | HCl salt 107–109.5° (ethanol. ether) | 1720 | 1.25(3H,t,J=7Hz), 1.40(3H,t,J=7Hz), 2.40(3H,s), 2.45(3H,s), 4.19(2H,m), 4.35(2H,q,J=7Hz), 6.26(1H,s), 7.47(1H,t,J=8Hz), 7.60(1H,d,J=7Hz), 8.14(1H,d,J=8Hz), 8.15(1H,s) | ① Calculated for C₂₄H₂₄N₆O₁₃ (picrirate):<br>C(%) H(%) N(%)<br>47.68 4.00 13.90<br>Found: 47.66 3.98 13.85 |
| 13 | R¹ = R² = ethyl<br>X = chloro<br>R = 3-nitrophenyl | 76 | crystals 97–98° (acetone. hexane) | 1730, 1690 | 1.27(3H,t,J=7Hz), 1.41(3H,t,J=7Hz), 2.48(3H,s), 4.23(2H,m), 4.38(2H,q,J=7Hz), 6.39(1H,s), 7.52(1H,t,J=8Hz), 7.64(1H,d,J=8Hz), 8.18(1H,d,J=8Hz), 8.19(1H,s) | ① Calculated for C₁₇H₁₈ClN₃O₆:<br>C(%) H(%) N(%)<br>51.58 4.58 10.62<br>Found: 51.73 4.53 10.72 |
| 14 | R¹ = ethyl<br>R² = X = methyl<br>R = 3-nitrophenyl | 52 | crystals 79–81° (ether. hexane) | 1720, 1710 1690 | 1.41(3H,t,J=7Hz), 2.39(3H,s), 2.46(3H,brs), 3.73(3H,s), 4.37(2H,q,J=7Hz), 6.27(1H,brs), 7.48(1H,t,J=8Hz), 7.60(1H,d,J=8Hz), 8.14(1H,d,J=8Hz), 8.16(1H,brs) | ② Calculated for C₁₇H₁₉N₃O₆:<br>361.1271<br>Found: 361.1260 |
| 15 | R¹ = R² = methyl<br>X-chloro<br>R = 3-nitrophenyl | 63 | crystals 128–129° (ethyl acetate. n-hexane) | 1735, 1700 | 2.48(3H,s), 3.78(3H,s), 3.95(3H,s), 6.40(1H,s), 7.52(1H,t,J=8Hz), 7.64(1H,d,J=8Hz), 8.17(1H,s), 8.18(1H,d,J=8Hz) | ② Calculated for C₁₅H₁₄ClN₃O₆:<br>367.0572<br>Found: 367.0583 |
| 16 | R¹ = ethyl<br>R² = methyl<br>X = chloro<br>R = 3-nitrophenyl | 57 | crystals 124–125° (ethyl acetate. n-hexane) | 1725, 1690 | 1.41(3H,t,J=7Hz), 2.48(3H,s), 3.77(3H,s), 4.38(2H,q,J=7Hz), 6.39(1H,s), 7.52(1H,t,J=8Hz), 7.63(1H,d,J=8Hz), 8.18(1H,d,J=8Hz), 8.20(1H,s) | ② Calculated for C₁₆H₁₆ClN₃O₆:<br>381.0725<br>Found: 381.0662 |
| 17 | R¹ = R² = X = methyl<br>R = 3-nitrophenyl | 60 | crystals 107–109° (ether) | 1700, 1680 | 2.39(3H,s), 2.46(3H,brs), 3.73(3H,s), 3.93(3H,s), 6.28(1H,brs), 7.47(1H,t,J=8Hz), 7.60(1H,d,J=8Hz), 8.13(1H,brs), 8.15(1H,d,J=8Hz) | ② Calculated for C₁₆H₁₇N₃O₆:<br>347.1114<br>Found: 347.1094 |
| 18 | R¹ = R² = ethyl<br>X = chloro<br>R = 4-methylthiophenyl | 37 | oil | 1720, 1690 | 1.25(3H,t,J=7Hz), 1.37(3H,t,J=7Hz), 2.44(3H,s), 2.46(3H,s), 4.19(2H,m), 4.33(2H,q,J=7Hz), 6.24(1H,s), 7.17(2H,d,J=9Hz), 7.23(2H,d,J=9Hz) | ② Calculated for C₁₈H₂₁ClN₂O₄S:<br>396.0911<br>Found: 396.0939 |
| 19 | R¹ = R² = ethyl<br>X = methyl<br>R = 4-methylthiophenyl | 80 | oil | 1720 | 1.23(3H,t,J=7Hz), 1.37(3H,t,J=7Hz), 2.37(3H,s), 2.42(3H,s), 2.42(3H,s), 2.45(3H,s), 4.15 (2H,q,J=7Hz), 4.31(2H,q,J=7Hz), 6.13(1H,s), 7.14(2H,d,J=9Hz), 7.20(2H,d,J=9Hz) | ② Calculated for C₁₉H₂₄N₂O₄S:<br>376.1454<br>Found: 376.1451 |
| 20 | R¹ = methyl<br>R² = ethyl<br>X = chloro<br>R = 4-methylthiophenyl | 13 | oil | 1730, 1690 | 1.25(3H,t,J=7Hz), 2.44(3H,s), 2.46(3H,s), 3.89(3H,s), 4.20(2H,q,J=7Hz), 6.24(1H,s), 7.19(2H,s), 7.20(2H,s) | ② Calculated for C₁₇H₁₉ClN₂O₄S:<br>382.0752<br>Found: 382.0717 |
| 21 | R¹ = X = methyl<br>R² = ethyl<br>R = 4-methylthiophenyl | 58 | oil | 1730, 1700 | 1.23(3H,t,J=7Hz), 2.37(3H,s), 2.42(3H,d,J=7Hz), 2.45(3H,s), 3.87(3H,s), 4.16(2H,q,J=7Hz), 6.13(1H,brs), 7.17(4H,s) | ② Calculated for C₁₈H₂₂N₂O₄S:<br>362.1297<br>Found: 362.1291 |
| 22 | R¹ = R² = ethyl<br>X = methyl<br>R = 2-chlorophenyl | 96 | crystals 78–79° (n-hexane) | 1730, 1710 | 1.23(3H,t,J=7Hz), 1.35(3H,t,J=7Hz), 2.42(6H,s), 4.14(2H,q,J=7Hz), 4.22–4.35(2H,m), 6.57(1H,s), 7.12–7.34(4H,m) | ① Calculated for C₁₈H₂₁ClN₂O₄:<br>C(%) H(%) N(%)<br>59.26 5.80 7.68<br>Found: 59.34 5.76 7.74 |

EXAMPLE 23

The coronary vascular dilative effect of 3N-substituted 3,4-dihydropryrimidine derivatives was tested.

TEST METHOD

Heartly guinea pigs (weight 400–500 g) were clubbed dead and their hearts were immediately isolated. The hearts were perfused with Krebs-Henseleit solution bubbled with a mixture of 95% $O_2$+5% $CO_2$ and maintained at 37° C. at a certain rate of 6 ml/minute according to Langendorff's method [J. Pharmacol. Methods 2, 143 (1979)]. The perfusion pressure was determined by a pressure transducer. Samples were prepared by dissolving 1 mg of a test compound in 1 ml of a mixture of dimethylsulfoxide and physiological saline (1:9) and diluting with physiological saline the solution to the predetermined concentration. 0.1 ml of the diluted solution was administered into the coronary artery via a rubber tube connected to an aorta cannula to obtain $ED_{50}$ (µg/heart) data as shown in Table 1. The numbers of the compounds in the Table correspond respectively to those of the working examples described above.

TABLE 1

| Compound (Ex. No.) | 1 | 2 | 3 | 4 | 5 | 6 | 7 | 8 | 9 | 10 | 11 |
|---|---|---|---|---|---|---|---|---|---|---|---|
| Pharmacological data $ED_{50}$ (µg/heart) | 0.055 | 0.98 | 1.45 | 0.25 | 0.066 | 0.70 | 0.40 | 0.033 | 0.78 | 0.75 | 1.65 |

| Compound (Ex. No.) | 12 | 13 | 14 | 15 | 16 | 17 | 18 | 19 | 20 | 21 | 22 |
|---|---|---|---|---|---|---|---|---|---|---|---|
| Pharmacological data $ED_{50}$ (µg/heart) | 1.9 | 0.48 | 1.1 | 2.8 | 10.0 | 2.5 | 0.37 | 0.58 | 0.22 | 1.0 | 0.086 |

As shown in Table 1, Compounds 1, 5, 8 and 22 have extremely strong coronary vascular dilative effects.

Since these compounds exhibit sufficient potency at a very low dose level, their side effects can be minimized to a negligible level.

EXAMPLE 24

The pharmacological effects of the compounds of the present invention with respect to the blood flow and blood vessel resistance of vertebral artery and systemic blood pressure (average pressure) in anesthetized dogs.

TEST METHOD

Male and female dogs (7–14 kg in weight) were induction-anesthetized with thiopental sodium (35 mg/kg, intraperitoneal), anesthetized with urethane (400 mg/kg, intravenous) and chloralose (60 mg/kg, intravenous) and kept under artificial respiration during the test. The first and second ribs were cut open to expose the left vertebral artery. A probe was attached to the origin of the artery and the blood flow was measured with an electromagnetic rheometer (Model MF-27, product of Nihon Koden K.K.)

At the same time, continuous measurement of the following parameters was made: systemic blood pressure (average pressure) at the right femoral artery, the ECG in the second induction period, the heart beat with a tachometer driven by the R wave, and the blood vessel resistance determined by loading a multiplication/division unit (EO-601 G, product of Nihon Koden K.K.) with the average values of blood pressure and blood flow in the vertebral artery. All of these parameters were recorded simultaneously on a polygraph (RM-600, product of Nihon Koden, K.K.)

All of the test compounds were injected through a cannula inserted into the femoral view.

TABLE 2

| Compound (Example No.) | Dose (mg/kg) | Numbers of cases | Average blood pressure | Vertebral artery blood flow | Vertebral artery vessel resistance |
|---|---|---|---|---|---|
| (4) | 0.001 | 3 | 95 ± 1 | 107 ± 4 | 91 ± 5 |
|  | 0.003 | 3 | 93 ± 1 | 113 ± 6 | 86 ± 7 |
|  | 0.01 | 3 | 91 ± 2 | 143 ± 12 | 66 ± 4 |
|  | 0.03 | 3 | 88 ± 1 | 147 ± 16 | 61 ± 5 |
|  | 0.1 | 3 | 84 ± 2 | 182 ± 16 | 51 ± 3 |
| (1) | 0.0003 | 3 | 94 ± 3 | 107 ± 4 | 93 ± 5 |
|  | 0.001 | 3 | 90 ± 1 | 115 ± 9 | 89 ± 4 |
|  | 0.003 | 3 | 88 ± 1 | 136 ± 6 | 72 ± 5 |
|  | 0.01 | 3 | 79 ± 3 | 172 ± 20 | 55 ± 3 |
|  | 0.03 | 3 | 74 ± 4 | 184 ± 26 | 50 ± 6 |
|  | 0.1 | 2 | 75 | 234 | 41 |
| (10) | 0.001 | 2 | 92 | 102 | 99 |
|  | 0.003 | 2 | 91 | 108 | 94 |
|  | 0.01 | 2 | 86 | 113 | 86 |
|  | 0.03 | 2 | 78 | 140 | 67 |
|  | 0.1 | 2 | 63 | 146 | 58 |
| (13) | 0.003 | 2 | 94 | 108 | 89 |
|  | 0.01 | 2 | 92 | 126 | 81 |
|  | 0.03 | 2 | 88 | 128 | 73 |
|  | 0.1 | 2 | 78 | 158 | 54 |
|  | 0.3 | 2 | 78 | 179 | 46 |
|  | 1.0 | 2 | 77 | 216 | 41 |
| (12) | 0.003 | 3 | 93 ± 0.3 | 129 ± 11 | 86 ± 2 |
|  | 0.01 | 3 | 86 ± 1 | 148 ± 3 | 73 ± 3 |
|  | 0.03 | 3 | 84 ± 3 | 163 ± 7 | 62 ± 4 |
|  | 0.1 | 3 | 77 ± 2 | 200 ± 6 | 47 ± 5 |
| (17) | 0.001 | 2 | 95 | 100 | 97 |
|  | 0.003 | 2 | 90 | 106 | 95 |
|  | 0.01 | 2 | 89 | 108 | 89 |
|  | 0.03 | 2 | 86 | 129 | 77 |
|  | 0.1 | 2 | 74 | 148 | 67 |
| (22) | 0.001 | 2 | 94 | 105 | 96 |
|  | 0.003 | 2 | 89 | 119 | 80 |
|  | 0.01 | 2 | 82 | 136 | 65 |
|  | 0.03 | 1 | 85 | 188 | 49 |
|  | 0.1 | 1 | 79 | 229 | 39 |
| (8) | 0.001 | 2 | 93 | 110 | 89 |
|  | 0.003 | 2 | 87 | 117 | 81 |
|  | 0.01 | 2 | 81 | 140 | 64 |
|  | 0.03 | 1 | 83 | 182 | 48 |
|  | 0.1 | 1 | 79 | 211 | 40 |
| Nifedipine | 0.0001 | 2 | 94 | 114 | 79 |
|  | 0.0003 | 2 | 94 | 129 | 67 |
|  | 0.001 | 2 | 87 | 154 | 57 |
| Nicardipine | 0.001 | 5 | 90 ± 1 | 123 ± 7 | 79 ± 4 |
|  | 0.003 | 5 | 87 ± 2 | 147 ± 15 | 67 ± 7 |
|  | 0.01 | 5 | 80 ± 2 | 183 ± 13 | 49 ± 3 |
| Papaverine | 0.1 | 7 | 93 ± 1 | 123 ± 4 | 78 ± 3 |
|  | 0.3 | 7 | 83 ± 3 | 151 ± 8 | 58 ± 3 |
|  | 1.0 | 7 | 73 ± 4 | 184 ± 14 | 43 ± 3 |

[NOTES]
[1] Percentages (%) are indicated as average ± standard error.
[2] Percentages (%) are represented as percentages of values after administration of test drugs to those before administration of the drugs.

As clearly shown in Table 2, the compounds of the present invention have substantially the same $Ca^{++}$ antagonistic effects as Nicardipine. Therefore, the compounds of the present invention are useful as agents for treating disorders of the cardiovascular system such as angina pectoris, arrhythmia, hypertension, asthma, brain circulation incompetence, arterial sclerosis and the like. This wide use of said compounds is based on the $Ca^{++}$ antagonistic effects. The compounds of the present invention are also expected to be used as carcinostatic agents.

What is claimed is:

1. A 3N-substituted 3,4-dihydropyrimidine compound of the formula:

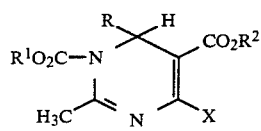

wherein $R^1$ is methyl or ethyl, $R^2$ is methyl or ethyl, R is phenyl, nitrophenyl, ($C_1$–$C_2$) alkylthiophenyl, chlorophenyl, bromophenyl, fluorophenyl, dichlorophenyl or trifluoromethyl, X is chloro or methyl and pharmaceutically acceptable acid addition salts thereof.

2. A composition for treating disorders of the cardiovascular system comprising an amount effective for treating disorders of the cardiovascular system of a 3N-substituted 3,4-dihydro-pyrimidine derivative of the formula:

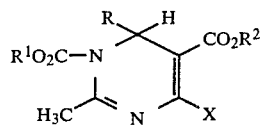

wherein $R^1$ is methyl or ethyl, $R^2$ is methyl or ethyl, R is phenyl, nitrophenyl, ($C_1$–$C_3$) alkylthiophenyl, chlorophenyl, bromophenyl, fluorophenyl dichlorophenyl, or trifluoromethyl, X is chloro or methyl or a pharmaceutically acceptable acid addition salt thereof; and a pharmaceutically acceptable carrier.

3. A composition according to claim 2 wherein R is phenyl, nitrophenyl, loweralkylthiophenyl, chlorophenyl, bromophenyl, fluorophenyl or dichlorophenyl.

4. A method for treating disorders of the cardiovascular system in a mammal comprising administering an effective amount of a 3N-substituted 3,4-dihydropyrimidine derivative of the formula:

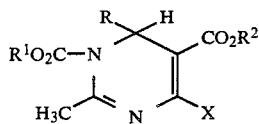

wherein $R^1$ is methyl or ethyl, $R^2$ is methyl or ethyl, R is phenyl, nitrophenyl, ($C_1$–$C_3$) alkylthiophenyl, chlorophenyl, bromophenyl, fluorophenyl, dichlorophenyl, or trifluoromethyl, X is chloro or methyl or a pharmaceutically acceptable acid addition salt thereof; and a pharmaceutically acceptable carrier.

* * * * *